United States Patent [19]

Paciello

[11] Patent Number: 5,041,574

[45] Date of Patent: Aug. 20, 1991

[54] PROCESS FOR THE PREPARATION OF PHOSPHINE CONTAINING COBALT CARBONYL COMPLEXES

[75] Inventor: Rocco A. Paciello, Wilmington, Del.

[73] Assignee: E. I. Du Pont de Nemours and Company, Wilmington, Del.

[21] Appl. No.: 564,145

[22] Filed: Aug. 9, 1990

[51] Int. Cl.$^5$ .............................................. C07F 15/06
[52] U.S. Cl. ....................................... 556/21; 556/20; 556/140; 556/141
[58] Field of Search ................... 556/20, 21, 138, 140, 556/141

[56] References Cited

U.S. PATENT DOCUMENTS 4,017,526  4/1977  Wilke et al. ..................... 556/140 X
4,497,737  2/1985  Sargeson et al. ................ 556/21 X
4,656,299  4/1987  Fujii et al. ..................... 556/140 X Primary Examiner—Arthur C. Prescott

[57] ABSTRACT

A process for the preparation of cobalt carbonyl complexes by heating a mixture containing an inert hydrocarbon solvent, at least one cobalt compound which is soluble in the reaction mixture, a trialkylphosphine, carbon monoxide, and a heterogeneous hydrogenation catalyst.

12 Claims, No Drawings

PROCESS FOR THE PREPARATION OF PHOSPHINE CONTAINING COBALT CARBONYL COMPLEXES

FIELD OF THE INVENTION

This invention relates to a process for the preparation of phosphine containing cobalt carbonyl complexes.

BACKGROUND OF THE INVENTION

Phosphine containing cobalt carbonyl complexes are disclosed in U.S. Pat. No. 3,715,405, and are known to be useful as catalysts in the hydrogenation of cyclododecatriene to produce cyclododecene. These complexes are prepared by reacting octacarbonyl cobalt and tri-n-butyl phosphine in benzene.

Another process for the preparation of these complexes is disclosed in Lanzhow Institute of Chemical Physics, Academia Sinica, Lanzhow, China, No. 2:141-2 (1986). This paper disclosed preparing these complexes by the reaction of $CaCO_3$, n-butyl phosphine, hydrogen and carbon monoxide at ca. 400 psi.

SUMMARY OF THE INVENTION

This invention is a process for the preparation of a cobalt complex having ligands of carbon monoxide and at least one ligand of phosphine per atom of cobalt, which comprises: forming a reaction mixture containing (a) an inert solvent, (b) at least one cobalt compound which is soluble in the reaction mixture, (c) a trialkylphosphine, (d) carbon monoxide, (e) hydrogen, and (f) a heterogeneous hydrogenation catalyst, heating the reaction mixture under pressure, and recovering the cobalt complex.

Suitable inert solvents for carrying out the process of the invention include hydrocarbons such as toluene, benzene, cyclododecatriene, xylenes, tetralin, or ethers, such as diethylether and tetrahydrofuran.

Suitable cobalt compounds include cobalt acetate hydrate, cobalt napthenoate, cobalt valerate, and cobalt 2-ethylhexanoate, or an insoluble cobalt compound that can be made soluble by the addition of a solubilizing agent. Such usually insoluble cobalt compounds include cobalt hydroxide, i.e. $Co(OH)_2$. Such compounds can be solubilized by use of a solubilizing agent such as a carboxylic acid, for example, valeric acid. Other carboxylic acids having 2 to about 10 carbon atoms are also believed suitable.

Suitable trialkylphosphines include those in which the alkyl group has from 1 to 8 carbon atoms. Preferred trialkylphosphines include normal butylphosphine, isobutylphosphine, secondary butylphosphine.

Suitable hydrogenation catalysts include those containing palladium and Raney cobalt. These catalysts may be contained on a suitable inert substrate, such as carbon, silica, or alumina. The amount of catalyst employed in the reaction will vary depending on the activity of the catalyst, but usually 0.5% to about 5% catalyst per weight of the reaction mixture is sufficient.

The process of the invention is carried out at a reaction temperature of about 100 deg C. and above, and at pressures of at least about 60 psi. One advantage of the process of the invention is that it is possible to operate at relatively mild temperatures and at relatively low pressures.

Hydrogen and carbon monoxide from any relatively pure source may be employed in the process. Usually these gases are employed in about equal molar amounts. It is usually desirable to have these gases present in the reaction mixture in excess of that theoretically necessary to react with all the cobalt compound employed.

The reaction proceeds relatively slowly, so reaction times of 2 to 15 hours are usually necessary to obtain complete reaction of the cobalt compound.

The reaction is best carried out with stirring and or agitation.

EXAMPLES

Example 1

Ingredients:
2.5 g $Co(OH)_2$
6 ml $P(n-Bu)_3$
0.5 ml Valeric Acid
0.5 g of Palladium on carbon, containing 5% by weight Palladium
75 ml toluene Loaded $Co(OH)_2$, one equivalent $P(n-Bu)_3$, 0.1 equivalent valeric acid, and the palladium on carbon catalyst to 75 ml toluene in a Fischer-Porter bottle with a mechanical stirrer. Pressured to 110 psi with a 1:1 mixture of $CO/H_2$. Heated to 100 deg C. with vigorous stirring. Solution turned dark red brown within 3 hours. An infrared spectrum of the solution showed one major carbonyl band at 1955 cm-1. However, some starting material was still observable and gas uptake continued. Repressured with 1:1 $CO/H_2$ and continued reaction. After 7-8 hours, gas uptake ceased. Repressurized with $H_2$ and ran for 10 total hours. Filtered solution, washed out reactor and frit with toluene. Removed volatiles under vacuum. Slurried dark red brown solid in petroleum ether, let mixture set at —40 deg C. overnight. Decanted and dried to yield dark red-brown blocks: 6.86 g first crop, 1.42 g second crop. Total isolated yield 89.2%. Infrared of product shows one major carbonyl band at 1955 cm$^-$ and the 31P NMR one signal at 52.8 ppm.

This analysis confirmed that the product was $Co_2(CO)_6(Pn-Bu_3)_2$.

Example 2

Ingredients:
0.5 g $Co(OH)_2$
0.29 g 5% Pd/C
1.33 ml $P(n-Bu)_3$
0.1 ml valeric acid
4 ml cyclododecatriene Loaded cobaltous hydroxide, 5% Pd/C (2.5% Pd/Co), $P(n-Bu)_3$, valeric acid, and cyclododecatriene in a Fischer-Porter tube with a stirbar. Pressured to 120 psi with $CO/H_2$ (1:1) and heated to 80 deg C. Ran infrared spectra of samples after 5, 8, 10, 12, and 14 hours.

Conversion of intermediate bands at 1910 and 1975 cm-1 to product band at 1955 cm-1 could be observed. Filtered.

31P NMR of reaction solution showed one major signal at 52.7 ppm. No free phosphine remained. This analysis confirmed that the product was $Co_2(CO)_6(Pn-Bu_3)_2$.

I claim:

1. A process for the preparation of a cobalt complex having ligands of carbon monoxide and at least one ligand of phosphine per atom of cobalt, which comprises: forming a reaction mixture containing (a) an inert solvent, (b) at least one cobalt compound which is soluble in the reaction mixture, (c) a trialkylphosphine, (d) carbon monoxide, (e) hydrogen, and (f) a heterogeneous hydrogenation catalyst, heating the reaction mixture under pressure, and recovering the cobalt complex.

2. The process of claim 1 in which the reaction mixture also contains a solubilizing agent for cobalt compounds that are normally insoluble in hydrocarbon solvents.

3. The process of claim 1 in which the cobalt compound is selected from the class consisting of cobalt acetate hydrate, cobalt napthenoate, cobalt valerate, and cobalt 2-ethylhexanoate, or an insoluble cobalt compound that can be made soluble by the addition of a solubilizing agent.

4. The process of claim 3 in which the solubilizing agent is a carboxylic acid.

5. The process of claim 2 in which the heterogeneous hydrogenation catalyst contains palladium or Raney cobalt.

6. The process of claim 3 in which the catalyst contains palladium, and the palladium is dispersed on an carrier substrate.

7. The process of claim 1 in which the trialkylphosphine is a tributylphosphine.

8. The process of claim 5 in which the reaction mixture is heated to about 100° C.

9. The process of claim 6 in which the reaction mixture is pressured to at least about 60 psi.

10. The process of claim 1 in which the cobalt complex is $Co_2(CO)_6(P\ butyl_3)_2$.

11. The process of claim 1 in which the carbon monoxide and the hydrogen are present in the reaction mixture in a molar ratio in the range of about 1:1 to about 1 to 4.

12. The process of claim 1 in which the inert solvent is selected from the class consisting of toluene, benzene, and cyclododecatriene.

* * * * *